(12) United States Patent
Etzler et al.

(10) Patent No.: US 6,849,777 B1
(45) Date of Patent: Feb. 1, 2005

(54) LNP, A PROTEIN INVOLVED IN THE INITIATION OF MYCORRHIZAL INFECTION IN PLANTS

(75) Inventors: Marilynn E. Etzler, Davis, CA (US); Nicholas J. Roberts, Palmerston North (NZ)

(73) Assignee: The Regents of the University of California, Oakland, CA (US)

( * ) Notice: Subject to any disclaimer, the term of this patent is extended or adjusted under 35 U.S.C. 154(b) by 151 days.

(21) Appl. No.: 09/657,631

(22) Filed: Sep. 6, 2000

(51) Int. Cl.[7] .................. C12N 12/29; C12N 15/82; A01H 1/00
(52) U.S. Cl. .................. 800/278; 800/287; 800/260; 536/23.6; 536/23.1; 536/24.1; 435/468
(58) Field of Search .................. 800/278, 287, 800/260, 290, 298; 536/23.6, 23.1, 24.1; 435/468, 419, 320.1

(56) References Cited

U.S. PATENT DOCUMENTS 6,465,716 B2 * 10/2002 Etzler et al. .................. 800/278

FOREIGN PATENT DOCUMENTS

WO          99/07223        *  2/1999

OTHER PUBLICATIONS

Bowie et al, Science 247:1306–1310, 1990.*
McConnell et al, Nature 411 (6838):709–713, 2001.*
Thomas et al teach (from WO 200052144, Sep. 8, 2000. sequence search results of DNA's encoding SEQ ID No.:10, Result 8).*
Bowie et al., Deciphering the Message in Protein Sequences: Tolerance to Amino Acid Substitutions, Mar. 16, 1990, Science, vol. 247, pp. 1306–1310.*

McConnell et al., Role of PHABULOSA and PHAVOLUTA in determining radial patterning in shoots, Jun. 7, 2001, Nature, vol. 411, pp. 709–713.*
Bauchrowitz, Martina A. et al.; "Lectin genes are expressed throughout root nodule development and during nitrogen–fixation in the *Rhizobium–Medicago* symbiosis"; 1996, *The Plant Journal*, vol. 9, No. 1, pp. 31–43.
Diaz, Clara L. et al.; "Root lactin as a determinant of host–plant specificity in the *Rhizobium*–legume symbiosis"; 1989, *Nature*, vol. 338, No. 6216, pp. 579–581.
Etzler, Marilynn E., et al.; "Do legume vegetative tissue lectins play roles in plant–microbial interactions?"; 1996, *Biology of Plant–Microbe Interactions, APS Press*, vol. 1, pp. 105–110.
Heidstra, Renze et al.; "Nod factor–induced host responses and mechanisms of Nod factor perception"; 1996, *New Phytologist*, vol. 133, No. 1, pp. 25–43.
Herve, C. et al.; "Characterization of an *Arabidopsis thaliana* gene that defines a new class of putative plant receptor kinases with an extracellular lectin–like domain"; 1996, *J. Mol. Biol.*, vol. 258, No. 5, pp. 778–788.
Hsieh, Hsu–Liang et al.; "Light–modulated abundance of an mRNA encoding a calmodulin–regulated, chromatin–associated NTPase in pea"; 1996, *Plant Molecular Biology*, vol. 30, pp. 135–147.
Roberts, Nicholas J. et al.; "Cloning and comparison of homologs to a cDNA encoding DB46, a nod factor binding lectin from *dolichos biflorus*"; 1997, *Plant Physiology*, vol. 114, No. 3, p. 288.
Schnell, Danny J. et al.; "Primary structure of the *Dolichos biflorus* seed lectin"; 1987, *The Journal of Biological Chemistry*, vol. 262, No. 15, pp. 7220–7225.

* cited by examiner

*Primary Examiner*—Elizabeth McElwain
*Assistant Examiner*—Stuart F. Baum
(74) *Attorney, Agent, or Firm*—Townsend & Townsend & Crew LLP

(57) ABSTRACT

The present invention provides LNP polynucleotides that are useful in modulating mycorrhizal infection in plants.

7 Claims, No Drawings

LNP, A PROTEIN INVOLVED IN THE INITIATION OF MYCORRHIZAL INFECTION IN PLANTS

CROSS-REFERENCES TO RELATED APPLICATIONS

The present application is related to U.S. Ser. No. 08/907,226, filed Aug. 6, 1997, and U.S. Ser. No. 08/129,112, filed Aug. 4, 1998, now U.S. Pat. No. 6,465,716, both of which are incorporated herein by reference.

STATEMENT AS TO RIGHTS TO INVENTIONS MADE UNDER FEDERALLY SPONSORED RESEARCH AND DEVELOPMENT

This invention was made with Government support under Grant No. GM21882, awarded by the National Institutes of Health, under Grant No. DCB 9004967, awarded by the National Science Foundation and under NRJCGP Grant number 97-35305-4630 from the United States Department of Agriculture. The Government has certain rights in this invention.

BACKGROUND OF THE INVENTION

Mycorrhizal associations are structures formed between symbiotic soil fungi and plant roots. Mycorrhizal fungi infect plant roots and enhance the plant's ability to take up water and nutrients, particularly phosphorus, from the soil. As obligate symbionts, mycorrhizal fungi are unable to live outside of a plant host.

It is estimated that more than 80% of flowering plant species on land are able to form mycorrhizal associations. Mycorrhizae fall into two groups based on the interacting plant hosts and fungal species. Woody Angiosperms and Gymnosperms interact with the fungi Basidiomycetes, Ascomycetes or Zygomycetes to form ectomycorrhizae. The Zygomycetes form endomycorrhizae with most other terrestrial plant species. Arbuscular mycorrhizae, an endomycorriza, are the most common form of mycorrhizae. Arbuscular mycorrhizal fungi interact nonspecifically with plants, and a single fungal species can symbiose with many plant species. (Gianinazzi-Pearson, V. The Plant Cell 8:1871–83 (1996); Harrison, M. J. Trends in Plant Science 2:54–60 (1997)). However, twenty percent of plants on land are unable to form or rarely form mycorrhizal associations, including the families Brassicaceae, Cyperaceae, Cruciferae, Chenopodiaceae, and Caryophyllaceae. (Raven, P. H., et al., BIOLOGY OF PLANTS. p.224, Worth Publishers, New York (1989); Sharma, S. et al. Microbiologia Sem. 13:427–436 (1997)).

Mycorrhizal associations provide a number of benefits to the host plant in addition to the well-documented enhancement of phosphate uptake. Mycorrhizal associations have been shown to stimulate uptake of nitrogen, zinc, copper, sulfur, potassium and calcium and to enhance the uptake of water. Mycorrhizal associations also protect the plant host from infection by pathogens. (Sharma, S. et al., Microbiologia Sem. 13:427–436 (1997)).

After infection with mycorrhizal fungi, crop plants exhibit improved growth. Economically important plants tested include vegetables, and field crops. See references in U.S. Pat. No. 5,096,481. Mycorrhizal fungal infection also enhances plant growth under stress conditions, including growth on reclaimed soils.

Previously, a root lectin, LNP (formerly called NBP46 or DB46) was isolated from young *Dolichos biflorus* root extracts. LNP is a 46 kDa protein that was isolated by affinity chromatography on hog gastric mucin blood group A+H substance conjugated to Sepharose (Quinn, J. M. and Etzler, M. E. Arch. Biochem. Biophys. 258:535–544 (1987)). The protein also has apyrase activity and appears to play an early role in rhizobium-legume biosynthesis (Etzler, M. E. et al., Proc. Natl. Acad. Sci. USA 96:5856–5861 (1999)). Genetic experiments indicate that the establishment of rhizobial symbiosis and mycorrhizal symbiosis share common steps (Albrecht, C. et al., EMBO J. 18:281–288 (1999)).

Identification of genes and proteins that modulate mycorrhizal fungal association with plants will further the beneficial use of mycorrhizal in agriculture. For example, plants that have enhanced mycorrhizal association will be able to use nutrients more efficiently and potentially require less fertilizer or be able to grow on less fertile soil. Plants that currently do not associate with mycorrhizal fungi could be transformed with genes to allow the association to take place, thereby increasing the range of environments for growth of these plants.

One of the obstacles to greater use of mycorrhizal fungi in agriculture is the difficulty in growing large quantities of the fungus. All mycorrhizal fungi are obligate symbionts and cannot be grown outside of the plant. Innoculants are most commonly made from the roots of infected plants. Enhancement of mycorrhizal fungal infection will improve the yield and efficacy of innoculant stocks. The present invention addresses these and other needs.

SUMMARY OF THE INVENTION

The present invention provides methods of modulating mycorrhizal infection in a plants. The method comprise introducing into the plant an expression cassette containing a plant promoter operably linked to a heterologous LNP polynucleotide or complement thereof, wherein the LNP polynucleotide encodes an LNP polypeptide at least about 70% identical to SEQ ID NO:2, SEQ ID NO:4, or SEQ ID NO:10. The heterologous LNP polynucleotide can be SEQ ID NO:1. SEQ ID NO:3, or SEQ ID NO:8.

The expression cassette can be introduced into the plant using any standard technique, including *Agrobacterium*-mediated transformation or through a sexual cross. In the expression cassette, the promoter can be linked to the LNP polynucleotide in an antisense or sense orientation.

Typically the methods are used to enhance expression of the LNP polynucleotide, thereby increasing infection of the plant by a mycorrhizal fungus. The method may further comprise infecting the plant with a mycorrhizal fungus, such as *Glomus intraradices*.

DETAILED DESCRIPTION OF THE INVENTION

1. Definitions

The phrase "mycorrhizal infection" refers to all interactions between mycorrhizal fungus and a transgenic plant. The term includes, but is not limited to, recognition between a plant polypeptide and structures on the fungus, binding of mycorrhizal fungi to the plant root, the symbiotic relationship between a mycorrhizal fungus and a plant, and mycorrhizal fungus-plant interactions, including any morphological or molecular changes initiated on interaction between the plant and the mycorrhizal fungus. The morphological changes can occur in either the plant or the mycorrhizal fungi and include specialized structures to facilitate exchange of nutrients between the plant and the fungi. For example, some species of mycorrhizal fungi form arbuscules and vesicles within plant cells. The molecular changes include, but are not limited to, signal transduction cascades that result in changes in expression of gene products. The changes of gene product expression may occur either transcriptionally or post-transcriptionally.

The phrase "isolated nucleic acid molecule" or "isolated protein" refers to a nucleic acid or protein which is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated LNP gene is separated from open reading frames which flank the gene and encode a protein other than LNP. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include Agrobacterium-mediated transformation, biolistic methods, electroporation, and the like. Such a plant containing the exogenous nucleic acid is referred to here as an R1 generation transgenic plant. Transgenic plants which arise from sexual cross or by selfing are descendants of such a plant.

The phrase "operably linked" refers to a functional linkage between a promoter and a second sequence, wherein the promoter sequence initiates transcription of RNA corresponding to the second sequence.

The term "polynucleotide," "polynucleotide sequence" or "nucleic acid sequence" refers to deoxyribonucleotides or ribonucleotides and polymers thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular LNP nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). The term nucleic acid is used interchangeably with gene, cDNA, and mRNA encoded by a gene.

An "LNP polynucleotide" is a nucleic acid sequence comprising (or consisting of) a coding region of about 100 to about 2000 nucleotides, sometimes from about 1400 to about 1500 nucleotides, which specifically hybridizes, to the *Dolichos biflorus* polynucleotide (SEQ ID NO:1), or to the *Lotus Japonicus* polynucleotide (SEQ ID NO:8), or to the *Medicago sativa* polynucleotide (SEQ ID NO:3), or which encodes an LNP polypeptide. The isolation and characterization of the *Lotus* and *Medicago* genes are described in the PCT application PCT/US98/16261.

An LNP polypeptide of the present invention comprises at least 50 amino acids, more preferably at least 100 amino acids, still more preferably at least 200 amino acids and most preferably up to about 500 amino acids from SEQ ID NO:2, SEQ thereof. The LNP polypeptides of the present invention also include proteins which have substantial identity to an LNP protein of at least 10 to 500 amino acids selected from SEQ ID NO:2, SEQ ID NO:4, and SEQ ID NO:10 SEQ ID NO:6 and conservatively modified variants thereof.

The term "sexual reproduction" refers to the fusion of gametes to produce seed by pollination. A "sexual cross" is pollination of one plant by another. "Selfing" is the production of seed by self-pollonization, i.e., pollen and ovule are from the same plant.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term LNP nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "LNP nucleic acid". In addition, the term specifically includes those sequences substantially identical (determined as described below) with an LNP polynucleotide sequence disclosed here and that encode polypeptides that are either mutants of wild type LNP polypeptides or retain the function of the LNP polypeptide (e.g., resulting from conservative substitutions of amino acids in the LNP polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60% identity. Altenatively, percent identity can be any integer from 60% to 100%, e.g. 60%, 61%, 62%, 63%, ect. More preferred embodiments include at least 60%, 65%, 70%, 75%, 80%, 85%, 90%, 95%, or 99% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point (Tm) for the specific sequence at a defined ionic strength pH. Low stringency conditions are generally selected to be about 15–30° C. below the Tm. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising LNP nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

The phrase "transgenic plant" refers to a plant into which heterologous polynucleotides have been introduced by any means other than sexual cross or selfing. Examples of means by which this can be accomplished are described below, and include *Agrobacterium*-mediated transformation, biolistic methods, electroporation, in planta techniques, and the like. Such a plant containing the heterologous polynucleotides is referred to here as an R1 generation transgenic plant. Transgenic plants may also arise from sexual cross or by selfing of transgenic plants into which heterologous polynucleotides have been introduced.

2. Introduction

The present invention provides polynucleotides referred to here as LNP polynucleotides, as exemplified by SEQ ID NO:1. Polypeptides encoded by the genes of the invention are lectins involved in binding a variety of carbohydrates. In addition, polypeptides function as an enzyme, catalyzing the dephosphorylation of nucleotide di- and triphosphates.

The polypeptides of the invention are also involved oligosaccharide signaling events that play important roles in the regulation of plant development, defense, and other interactions of plants with the environment. Although the structures of some of these oligosaccharides have been characterized in the prior art, little is known about the plant receptors for these signals, nor the mechanism(s) by which these signals are transduced.

Without wishing to be bound by theory, it is believed that polypeptides of the LNP protein modulate oligosaccharide signaling events that are important for the interaction between mycorrhizal fungi and plants. Mycorrhizal associations are known to enhance phosphate uptake by plants. The LNP protein also has apyrase activity. Thus, LNP may also be involved in the enhancement of phosphate uptake after infection by mycorrhizal fungi.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook, et al.

3. Isolation of Nucleic Acid Sequences from Plants

The isolation of sequences from the genes of the invention may be accomplished by a number of techniques. For instance, oligonucleotide probes based on the nucleic acid and peptide sequences disclosed herein can be used to identify the desired gene in a cDNA or genomic DNA library from a desired plant species. To construct genomic libraries, large segments of genomic DNA are generated by random fragmentation, e.g., using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared from the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes known to those of skill.

Appropriate primers and probes for identifying LNP genes from *Dolichos biflorus* or transgenic plant tissues are generated from comparisons of the sequences provided herein. For a general overview of PCR see PCR PROTOCOLS: A GUIDE TO METHODS AND APPLICATIONS, (Innis, M, Gelfand, D., Sninsky, J. and White, T., eds.), Academic Press, San Diego (1990). Appropriate degenerate primers for this invention include, for instance: a 5' PCR primer [5'TA(T/C)GCNGTNAT(T/C)TT(T/C)GATGC-3'] (SEQ ID NO:13) and a 3' PCR primer [5'-AT(A/G)TT(A/G)TA(T/A/G)AT(G/A)CCNGG-3'] (SEQ ID NO:14) where N denotes all nucleotides. The amplification conditions are typically as follows. Reaction components: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per mL Taq polymerase. Program: 96° C. for 3 min., 30 cycles of 96° C. for 45 sec., 50° C. for 60 sec., 72° C. for 60 sec, followed by 72° C. for 5 min.

Using the above primers, a partial coding sequence will be obtained. There are many techniques known to those of skill to determine and isolate the complete coding sequence. These methods include using the PCR amplified subsequence to probe a cDNA library for longer sequences.

A preferred method is RACE (Frohman, et. al., *Proc. Nat'l. Acad. Sci. USA* 85:8998 (1988)). Briefly, this technique involves using PCR to amplify a DNA sequence using a random 5' primer and a defined 3' primer, e.g., (5' RACE) or a random 3' primer and a defined 5' primer, e.g., (3' RACE). The amplified sequence is then subcloned into a vector where it is then sequenced using standard techniques. Kits to perform RACE are commercially available (e.g. 5' RACE System, GIBCO BRL, Grand Island, N.Y., USA). In this manner, the entire LNP coding sequence of about 1600 bp can be obtained (SEQ ID NO:1). The invention also provides genomic sequence of the LNP (SEQ ID NO:3).

Alternatively, primers can be selected and synthesized by those of skill from the cDNA sequence disclosed in SEQ ID NOs:1 and 3.

Polynucleotides may also be synthesized by well-known techniques as described in the technical literature. See, e.g., Carruthers, et al., *Cold Spring Harbor Symp. Quant. Biol.* 47:411–418 (1982), and Adams, et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

4. Use of Nucleic Acids of the Invention to Modulate Gene Expression

The polynucleotides of the invention can be used to enhance expression (i.e., increase expression of an endogenous gene or provide LNP expression in a plant that does not normally express LNP) of genes of the invention and thereby enhance infection of transgenic plants by mycorrhizal fungi, increase the level of nutrients taken up by the plants, and affect the growth and development of transgenic plants. Alternatively, enhanced expression can be used to modulate oligosaccharide signaling in the plant. This can be accomplished by the overexpression of LNP polypeptides in the tissues of transgenic plants.

The heterologous LNP polynucleotides do not have to code for exact copies of the LNP proteins exemplified herein. Modified LNP polypeptide chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et al., *Meth. Enzymol.* 194: 302–318 (1991)). For example, the chains can vary from the naturally occurring sequence at the primary structure level by amino acid substitutions, additions, deletions, and the like. These modifications can be used in a number of combinations to produce the final modified protein chain.

Alternatively, the nucleic acid sequences of the invention can be used to inhibit expression of an endogenous gene. One of skill will recognize that a number of methods can be used to inactivate or suppress LNP activity or gene expression. The control of the expression can be achieved by introducing mutations into the gene or using recombinant DNA techniques. These techniques are generally well known to one of skill and are discussed briefly below.

Methods for introducing a genetic mutations into a plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Desired mutants are selected by assaying for increased seed mass, oil content and other properties.

Gene expression can be inactivated using recombinant DNA techniques by transforming plant cells with constructs comprising transposons or T-DNA sequences. LNP mutants prepared by these methods are identified according to standard techniques. For instance, mutants can be detected by PCR or by detecting the presence or absence of LNP mRNA, e.g., by Northern blots. Mutants can also be selected by assaying for increased seed mass, oil content and other properties.

The isolated sequences prepared as described herein, can also be used in a number of techniques to suppress endogenous LNP gene expression. A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801,340.

The nucleic acid segment to be introduced generally will be substantially identical to at least a portion of the endogenous LNP gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

Catalytic RNA molecules or ribozymes can also be used to inhibit expression of LNP genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323,5,231,020, and 5,283,184. In addition, a combination of simultaneous sense and antisense expression can also be used for gene silencing in plants (Waterhouse et al. *Proc. Natl. Acad. Sci. U.S.A.* 95: 13959–13964 (1998).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

A. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising, et al., *Ann. Rev. Genet.* 22:421–477 (1988). A DNA sequence coding for the desired polypeptide, for example a cDNA sequence encoding the full length LNP protein, will preferably be combined with transcriptional and translational initiation regulatory sequences which will direct the transcription of the sequence from the gene in the intended tissues of the transgenic plant, i.e., a root-specific promoter.

Promoters can be identified by analyzing the 5' sequences of a genomic clone in which naturally occurring lectin nucleotide phosphohydrolase genes, i.e., LNP, can be found. At the 5' end of the coding sequence, nucleotide sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing, et al., in GENETIC ENGINEERING IN PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell* 1:855–866 (1989); Bustos, et al., *Plant Cell* 1:839–854 (1989); Green, et al., *EMBO J.* 7:4035–4044 (1988); Meier, et al., *Plant Cell* 3:309–316 (1991); and Zhang, et al., *Plant Physiology* 110:1069–1079 (1996)).

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the instant invention in a specific tissue (tissue-specific promoters) or may be otherwise under more precise environmental control (inducible promoters). Examples of tissue-specific promoters under developmental control include promoters that initiate transcription only in certain tissues, such as roots, fruit, seeds, or flowers. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta. Other markers such as green fluorescence protein (GFP), GUS or luciferase can also be used.

B. Production of Transgenic Plants

DNA constructs of the invention may be introduced into the genome of a desired plant host by a variety of conventional techniques. For example, the DNA construct may be introduced directly into the genomic DNA of a plant cell using techniques such as electroporation and microinjection of plant cell protoplasts, or the DNA constructs can be introduced directly into plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *EMBO J.* 3:2717–2722 (1984). Electroporation techniques are described in Fromm, et al., *Proc. Nat'l. Acad. Sci. USA* 82:5824 (1985). Ballistic transformation techniques are described in Klein, et al., *Nature* 327:70–73 (1987).

*Agrobacterium tumefaciens*-mediated transformation techniques, including disarming and use of binary vectors, are well described in the scientific literature. See, for example Horsch, et al., *Science* 233:496498 (1984), and Fraley, et al., *Proc. Nat'l. Acad. Sci. USA* 80:4803 (1983).

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York (1983); and Binding, REGENERATION OF PLANTS, PLANT PROTOPLASTS, pp. 21–73, CRC Press, Boca Raton (1985). Regeneration can also be obtained from plant callus, explants, organs, or parts thereof. Such regeneration techniques are described generally in Klee, et al., *Ann. Rev. of Plant Phys.* 38:467–486 (1987).

To determine the presence of a reduction or increase of LNP activity, a variety of assays can be used including enzymatic, immunochemical, electrophoretic detection assays (either with staining or western blotting), or complex carbohydrate binding assays.

In a preferred embodiment, a competitive solid phase assay is used to measure LNP activity (Etzler, M. E., *Glycoconj. J.* 11:395 (1994)). This assay measures the ability of various ligands to inhibit the binding of labeled LNP protein to pronase-digested hog gastric mucin blood group A+H substance (HBG A+H) conjugated to Sepharose® (Quinn, J. M. & Etzler, M. E., *Arch. Biochem. Biophys.* 258:535 (1987)).

In another preferred embodiment, an apyrase assay is used to measure LNP activity. See Etzler et al., *Proc. Natl. Acad. Sci. USA* 96:5856–5861 (1999) and Drueckes, P. et al., *Anal. Biochem.* 230:173–177 (1995). This assay measures the ability of the enzyme to dephosphorylate nucleoside di- and tri-phosphates.

The nucleic acids of the invention can be used to confer desired traits on essentially any plant. Thus, the invention has use over a broad range of plants, including species from the genera *Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Effects of gene manipulation can be observed by northern blots of the mRNA isolated from the tissues of interest. Typically, if the amount of mRNA has increased, it can be assumed that the gene is being expressed at a greater rate than before. Other methods of measuring LNP expression would be by measuring the mycorrhizal infection of the transgenic plants. In addition, levels of LNP could be measured immunochemically, i.e., ELISA, RIA, EIA and other antibody based assays well known to those of skill in the art.

5. Inoculation of Transgenic Plants with Mycorrhizal fungi. Currently, mycorrhizal inoculation of plants can be done on a small scale. Methods used to cultivate mycorrhizal fungi include isolation of spores from soil, pot culture from a single spore to produce colonized root inoculum, and hydroponic or aeroponic methods to grow mycorrhizal plants. Infection of plants with mycorrhizal fungi is know to those of skill in the art. (U.S. Pat. No. 5,096,481, incorporated by reference; Sharma, S. *Microbiogia Sem.* 13:427–436 (1997); Sylvia, D. Vesicular-Arbuscular Mycorrhizal Fungi in Methods of Soil Analysis Part 2 (1994)); Mycorrhizal cultures can be purchased commercially from International Culture Collection of Arbuscular and Vesicular-Arbuscular Mycorrhizal Fungi (Morgantown, W.Va., USA) and Tree of Life (San Juan, Calif., USA).

6. EXAMPLES

The following examples are offered to illustrate, but not to limit the claimed invention.

Example 1

Characterization of Mycorrhizal Infection in the Absence of LNP Expression

Generation of Stable *Lotus japonicus* Transformants that Express Antisense LNP.

Antisense technology was used in the model legume, *Lotus japonicus*, to test the hypothesis that a novel lectin/nucleotide phosphohydrolase (LNP) is involved in the early events that lead to rhizobial-legume and mycorrhizal-legume symbioses. Antisense lines with no detectable LNP on the surface of the root were unable to undergo root hair deformation and nodulation in response to symbiotic rhizobia. These lines also displayed a severe reduction in ability to colonize with mycorrhizae. The data suggest that in *Lotus japonicus* LNP plays a role in an initial step of both symbioses.

The initiation of the nitrogen-fixing Rhizobium-legume symbiosis depends upon specific recognition events that occur between the roots of a particular legume species and the rhizobial strains capable of nodulating that species. Lipochitooligosaccharide signals, called Nod factors (J. Dénarié, F. Debellé, 1-C. Promé, *Ann. Rev. Biochem.* 65:503 (1996); S. R. Long, *Plant Cell* 8:2885 (1996)), produced by the rhizobia have been found to play a key role in this process (P. Mylona, K. Pawlowski, T. Bisseling, *Plant Cell* 7: 869 (1995); J. Cohn, R. B. Day, G. Stacey, *Trends Pl.* Sci. 3:105 (1998)). These signals induce a number of responses in the legume roots that lead to the formation of the root nodules in which the symbioses occur. These responses and the identification of Nod factor binding sites in root membranes (A. Niebel, F. Gressent, J. J. Bono, R. Ranjeva, J. Cullimore, *Biochimie* 81:669 (1999)) imply the existence of Nod factor receptors and an accompanying signal transduction mechanism (J. A. Downie, S. A. Walker, *Current Opinion in Plant Biology* 2:483 (1999)). It has been proposed that some elements of such a plant response mechanism may also play a role in establishing the mycorrhizal-legume symbiosis (V, Gianinaazi-Pearson. *Plant Cell* 8:1871 (1996); M. J. Harrison, *Trends Plant Sci.* 2:54 (1997); C. Albrecht, R. Geurts, T. Bisseling, *EMBO Journal* 18, 281 (1999)). Evidence for this involvement includes the existence of legume mutants that are unable to form either of these symbioses (S. M. Bradbury, R. L. Peterson, S. R. Bowley, *New Phytol.* 124:665 (1993); B. Balaji, A. M. Ba, T. A. LaRue, D. Tepfer, Y. Piché, *Plant Sci.* 102:195 (1994); E. Wegel, L. Schauser, N. Sandal, J. Stougaard, M. Parniske, *MPMI.* 11:933 (1998)) and the induction of early nodulin genes during the colonization of roots by mycorrhizae (C. Albrecht, R. Geurts, T. Bisseling, *EMBO Journal* 18, 281 (1999); P. van Rhijn et al., *Proc. Natl. Acad. Sci. U.S.A.* (USA) 94:5467 (1997)). However, legume genes essential for establishing both of these symbioses have yet to be identified.

A novel lectin with apyrase activity from the roots of the legume, *Dolichos biflorus*, is able to bind Nod factors (M. E. Etzler et al. *Proc. Natl. Acad. Sci. U.S.A.* (USA) 96:5856 (1999)). This lectin nucleotide phosphohydrolase (LNP) is present on the epidermal cell surface of roots and root hairs in the region of rhizobial attachment. Preincubation of the roots with an antiserum made against recombinant LNP inhibited rhizobial-induced root hair deformation and nodulation. LNP orthologues in other legumes have also been identified. Sequence comparisons with animal and plant apyrases, including other legume apyrases, show that the LNPs appear to constitute a specialized category of apyrases that may be unique to the legumes (N. J. Roberts et al., *Molecular and General Genetics* 262:261(1999)). These correlative studies suggested that LNPs may play a role in the initiation of the Rhizobium-legume symbiosis. In the absence of a null mutant to test the possible involvement of LNP in both the Rhizobium-legume and Mycorrhizae-legume symbioses, antisense technology was utilized in the model legume, *Lotus japonicus* (K. Handberg and J. Stougaard, *Plant J.* 2: 487(1992); Q. Jiang, P. M. Gresshoff, *MPMI* 10:59(1997)) to assess the role(s) of this protein.

Three different Lj-LNP antisense constructs were used to generate stable transformants of *L. japonicus*. There was no distinguishable phenotypic growth difference between the wild type and transgenic lines when the plants were grown in the presence of nitrate and ammonia. The ability of the roots to form nodules was tested by inoculating the plants with *Mesorhizobium loti*, a symbiont of *L. japonicus*. Two independent antisense lines, 5'-D-1 and 5'-R-4, formed no nodules with *M. loti*; whereas the other antisense lines and the vector control plants formed healthy nodules (Table 1). Immunoblot analysis of the roots of the transgenic lines revealed that the Nod+ transgenic lines generally had wild type levels of a single immunoreactive band of the predicted size of Lj-LNP whereas the two Nod transgenic lines had substantially reduced levels. Confocal immunofluoresence microscopy showed that in contrast to the wild type and the Nod+ antisense lines the two Nod lines had no detectable LNP on the surface of the root or root hairs.

Southern blot analyses of the 5'-D-1 and 5'-R-4 Nod plants showed that both lines have multiple copies of the antisense transgene. Analysis of the 5'-D-1 T1 generation suggests that the expression of the selectable marker (nptII) and the Nod phenotype segregate together. Cosegregation of these traits, coupled with the generation of 2 independent Nod antisense lines, indicates that the Nod phenotype is unlikely to be due to insertional or somatic mutation.

Further examination of the 5'-D-1 Nod⁻ line revealed that after growth in the presence of rhizobia for 4 weeks these plants had numerous root hairs that exhibited a branched or wavy morphology. To investigate the effect of the rhizobia on root hair morphology seedlings were grown in the presence and absence of rhizobia for 4 days (normally a sufficient period of time to see rhizobial-induced root hair deformations). The young and emerging root hairs on the 5'-D-1 Nod plants were almost exclusively straight, whereas typical 'Shepherd's crook' structures were present on both individual and groups of emerging and young root hairs of the wild-type plants. These data suggest that LNP plays a role in the initiation of the Rhizobium-legume symbiosis in a process either prior to, and/or including the process of root hair deformation.

Characterization of Mycorrhizal Infection of *L. japonicus* Lines that Express Antisense LNP.

To test if LNP is also involved in the mycorrhizal-legume symbiosis, wild type, two of the Nod⁻ lines (5'-D-1 and 5'R) and 3 of the Nod+ LNP antisense lines with *Glomus intraradices*, a symbiont of *L. japonicus*. In the 5'-D-1 Nod⁻ line less than 6% of root segments were infected, as compared to the infection of approximately 89% of root segments in wild type and Nod+ transgenic lines (Table 1). On average the shoots of the 5'-D-1 Nod line were 30% shorter than the shoots of the other inoculated plants. The few roots of the 5'-D-1 Nod line that were colonized had a density of vesicles very similar to the wild type. A similar result was reported with *L. japonicus* Myc mutants (E. Wegel, L. Schauser, N. Sandal, J. Stougaard, M. Parniske, *MPMI*. 11:933 (1998)) where the mutants had greatly reduced numbers of colonized roots but the subsequent development of the successful mycorrhizae appeared to be normal. Previously we suggested that LNPs are unique to the legumes (N. J. Roberts et al., *Molecular and General Genetics* 262:261 (1999)); if this hypothesis is correct then either the non-leguminous Myc+ plants have a protein that performs a similar function in the mycorrhizal symbiosis or the legumes have uniquely modified the process to involve LNP.

In addition to LNP, legume plants contain other apyrases that more closely resemble the apyrases found in nonleguminous plants. One such conventional apyrase is expressed in *L. japonicus* roots. The relatively high degree of sequence conservation between LNPs and conventional apyrases prompted a comparison of the levels of transcript of this conventional apyrase in the plant lines used in this study. Northern blot analysis showed the level of this conventional apyrase is approximately equal in wild-type, control and antisense lines, thus establishing that the antisense constructs did not affect the transcript level of this conventional apyrase.

In the absence of detectable LNP on the surface of the root and young and emerging root hairs, *L. japonicus* is Nod⁻ and has greatly reduced mycorrhizal association. This finding suggests that in *L. japonicus* LNP plays a role in both these symbioses. The lack of root hair deformation in the Nod⁻ line after 4 days in the presence of rhizobia indicates that LNP acts upstream of the recently discovered Nin gene, which encodes a reputed transcription factor believed to be involved in the formation of infection threads and initiation of nodule primordia (L. Schauser, A. Roussis. J. Stiller, J. Stougaard, *Nature* 402:191 (1999)).

TABLE 1

Nodulation and growth data of wild-type and transgenic plants 4 weeks after inoculation with *M. loti*; % of wild-type and transgenic root segments with vesicles 6 weeks after inoculation with *G. intraradices*. Standard deviations are included for all averages.

| | | Inoculated with *M. loti* | | | Inoculated with *G. intraradices* % Root |
|---|---|---|---|---|---|
| Line | Generation | Number of Nodules per Plant[a] | Shoot Mass (mg) per Plant | Root Mass (mg) per Plant | Segments With Vesicles |
| wild type | F10 | 23.7 ± 3.2 | 18.7 ± 4.4 | 10.2 ± 2.7 | 87.9 ± 3.0 |
| pBIN19 | T1 | 13.3 ± 2.4 | 15.0 ± 1.4 | 8.0 ± 0.4 | ND |
| FL-F-3-1 | T2 | 12.9 ± 1.3 | 9.5 ± 3.1 | 5.8 ± 1.4 | 88.6 ± 1.3 |
| FL-F-3-2 | T2 | 14.8 ± 2.4 | 13.0 ± 3.8 | 7.2 ± 1.8 | ND |
| 3'-A | T3 | 12.2 ± 0.7 | 6.9[b] ± 1.7 | 5.1[b] ± 1.0 | ND |
| 3'-B | T3 | 15.3 ± 3.5 | 11.3 ± 2.5 | 6.7 ± 1.4 | 87.9 ± 3.6 |
| 3'-E | T2 | 20.3 ± 1.7 | 13.9 ± 4.2 | 6.8 ± 1.9 | ND |
| 5'-D-1 | T3 | 0.0 ± 0.0 | 8.3 ± 0.2 | 6.0 ± 0.7 | 5.5 ± 2.7 |
| 5'-D-2 | T3 | 25.5 ± 1.4 | 20.4 ± 1.8 | 11.0 ± 0.7 | 90.6 ± 3.5 |
| 5'-H | T2 | 17.8 ± 1.1 | 16.9 ± 1.4 | 8.4 ± 0.4 | ND |
| 5'-K | T2 | 14.5 ± 0.9 | 10.6 ± 1.9 | 5.8 ± 1.0 | ND |
| 5'-R | T2 | 0.0 ± 0.0 | 5.9 ± 1.3 | 6.1 ± 0.2 | 5.4 ± 1.4 |

[a]The average nodule number per plant was calculated using each complete pot as a single replicate. On average the Nod+ transgenic lines had fewer nodules than wild-type. It is of interest that a general reduction in nodule number compared to wild-type was also reported in unrelated transgenic kanamycin resistant Lotus plants [P, van Rhijn, R.B. Goldberg, A.M. Hirsch, Plant Cell 10, 1233 (1998)].
[b]This line was stunted under conditions lacking nitrogen.
ND. Not determined.

Methods

Construction of LNP antisense vectors. Full-length (FL), 5' and 3' antisense constructs were generated using Lj-LNP cDNA (N. J. Roberts et al., *Molecular and General Genetics* 262, 26 I (1999)). These constructs contained nucleotides 1–1489 (FL), nucleotides 1–719 (5') and nucleotides 536–1383 (3'). Each cDNA segment was cloned into the Xba I site of the shuttle vector pDH5 1 [J. L. Pietrzak, RD. Shillito, T. Hohn, I. Potrykus, *Nuc. Ac. Res.* 14, 5857 (1986)] in the reverse orientation relative to the CaMV35S promoter and terminator. The antisense cassette was purified from pDH51 after EcOR I digestion and ligated into the EcOR I site of the binary vector pBIN19 which utilizes nptII as a selectable kanamycin resistance marker under the control of the Nos promoter (M. W. Bevan, *Nuc. Ac. Res.* 12, 8711 (1984)).

Generation of *L. japonicus* lines expressing antisense LNP. The three antisense constructs and a vector control (pBIN19) were transformed into *Agrobacterium tumefaciens*, strain AGL1 (G. L. Lazo, P. A. Stein, R. A. Ludwig, *Bio/Technology* 9, 963 (1991)), and used to transform *L. japonicus* hypocotyls according to the procedure described by Stiller et al., *J. Exp. Bot.* 48, 1357 (1997) with the following modifications: a) plants were grown on regeneration medium for only 4–5 days until visible swelling was observed; b) no geneticin was used once the callus was placed on shoot induction medium; and c) full strength cefotaxime was utilized to control agrobacterial growth on all shoot and root media. On some lines successful root initiation was only achieved using the higher auxin concentration in the hairy root regeneration protocol. Regenerated plants were grown under greenhouse conditions and seeds were tested for geneticin resistance on phytagel plates containing 5 μg/ml geneticin, 1% sucrose, 1× Gamborg's B5 medium (O. L. Gamborg, R. A. Miller, K, Ojima, *Exp. Cell Res.* 50, 151(1968)). Each of the T0 and subsequent T1 and T2 plants and their seed lines were subjected to Southern blot analyses. Three independent 3' antisense lines (3'-A, B, & E), five independent 5' antisense lines (5'-D1, D2, H. K & R), two FL lines (FL-F-3-1 & 2) and a vector control (pBIN19) were selected for nodulation assays.

Inoculation of *L. japonicus* LNP-antisense lines with *Mesorhizobium loti*. Four days after germination approximately 50 uniform seedlings from each line were transferred to pots (10×10×8 cm) containing sterile vermiculite and perlite (1:1, V/V). The seedlings were grown for 6 more days and then thinned to approximately 8 plants per pot to maintain uniformity. Four pots from each line were inoculated with 50 ml/pot of a fresh overnight culture of *M. loti* diluted to $10^5$ cells/ml in Hoagland's solution lacking nitrogen (D. R. Hoagland, D. I. Arnold, Calif Agric. Expt. Sta. Cir. 347, College of Agriculture, Univ. of Calif. Berkeley, Calif. (1950)). Preliminary experiments established that this concentration of rhizobia results in approximately a maximum number of nodules/plant. One pot per line was used as an uninoculated control. The distribution of each inoculated pot was randomized in the growth chamber and the plants were grown for 4 weeks using a 26° C., 16 hr day (350 μM $m^{-2}$ $S^{-1}$), 22° C., 8 hr night. The plants were watered daily using sterile water that was supplemented weekly with sterile Hoagland's solution lacking nitrogen. Four weeks after inoculation the plants were gently removed from the soil, washed and the number of visible nodules were counted on each plant. The shoot and root material in each pot were separated and dried at 65° C. for 2 days prior to weighing.

Inoculation of *L. japonicus* LNP antisense lines with *Glomus intraradices*. The ability to be colonized by the mycorrhizae was tested using 2 independent *Glomus intraradices* sources, International Culture Collection of Arbuscular and Vesicular-Arbuscular Mycorrhizal Fungi (Morgantown, W.Va., USA) and Tree of Life (San Juan, Calif., USA). Inoculum was mixed with sterile vermiculite (1:9 VA'), seeds were germinated on the surface of these mixes in duplicate pots. The plants were watered daily with sterile water that was supplemented weekly with sterile Hoagland's solution 2 containing 20 μM $NH_4H_2PO_4$, pH 6.8. Plants were grown under similar conditions to the nodulation experiment for approximately 6 weeks. Plants were gently removed from the soil and washed. The roots were separated from the shoots and cleared in 2.5% KOH at 90° C. for 90 minutes, rinsed in distilled water then acidified in 1% HCl for 60 minutes prior to staining in Trypan blue at 90° C. for 1 hour and destained overnight in 50% glycerol. Roots were cut into approximately 1 cm segments and arranged in parallel on glass slides. The presence or absence of vesicles was analyzed using a compound microscope by viewing each segment once over a 2.1 mm field of view.

What is claimed is:

1. A method of increasing mycorrhizal infection in a plant, the method comprising introducing into the plant an expression cassette containing a plant promoter operably linked to a heterologus LNP polynucleotide or complement thereof and infecting the plants with mycorrhizal fungi, wherein the LNP polynucleotide encodes an LNP polypeptide at least about 70% identical to SEQ ID NO:10 and functions as a Nod factor binding protein.

2. The method of claim 1, wherein the heterologous LNP polynucleotide is SEQ ID NO: 8.

3. The method of claim 1, wherein the plant promoter is from an LNP gene.

4. The method of claim 1, wherein the expression cassette is introduced into the plant through a sexual cross.

5. The method of claim 1, wherein the LNP polynucleotide is operably linked to the promoter in sense orientation.

6. The method of claim 1, wherein the mycorrhizal fungus is *Glomus intraradices*.

7. The method of claim 1, wherein the LNP polypeptide is SEQ ID NO:2 or SEQ ID NO:4.

* * * * *

SEQUENCE LISTING

```
<160> NUMBER OF SEQ ID NOS: 14

<210> SEQ ID NO 1
<211> LENGTH: 1643
<212> TYPE: DNA
<213> ORGANISM: Dolichos biflorus
<220> FEATURE:
<221> NAME/KEY: CDS
<222> LOCATION: (51)..(1439)
<223> OTHER INFORMATION: lectin nucleotide phosphohydrolase (LNP, NBP46
      or DB46) root lectin
<221> NAME/KEY: mat_peptide
<222> LOCATION: (195)..(1436)

<400> SEQUENCE: 1
gaaactgaaa cgagtactct ttcagtggtg aggttctgag agattcagaa atg aat         56
                                                        Met Asn tgg gtg tgg cca aag aca aag agc atg agc ttc cta ctc ctc atc act      104
Trp Val Trp Pro Lys Thr Lys Ser Met Ser Phe Leu Leu Leu Ile Thr
    -45             -40                 -35 ttt cta ctc ttc tca ttg cca aaa ctt tct tct tcg caa tat gtt ggg      152
Phe Leu Leu Phe Ser Leu Pro Lys Leu Ser Ser Ser Gln Tyr Val Gly
-30             -25                 -20                 -15
```

```
aac agt atc tta cta aat cat cgt aag ata ctt ccc aac cag gaa ctc      200
Asn Ser Ile Leu Leu Asn His Arg Lys Ile Leu Pro Asn Gln Glu Leu
            -10                 -5                  -1  1 ctt acc tct tac gct gtc atc ttt gat gct ggt agc tct ggg agt cgt      248
Leu Thr Ser Tyr Ala Val Ile Phe Asp Ala Gly Ser Ser Gly Ser Arg
         5                  10                  15 gtc cat gtc ttc aat ttt gac cag aac tta gat ctc ctg cac att ggc      296
Val His Val Phe Asn Phe Asp Gln Asn Leu Asp Leu Leu His Ile Gly
     20                  25                  30 aat gac ctc gag ttt aca aaa aag atc aaa ccc ggt ttg agc tca tac      344
Asn Asp Leu Glu Phe Thr Lys Lys Ile Lys Pro Gly Leu Ser Ser Tyr
 35                  40                  45                  50 gct gat aag cct gaa aaa gct gca gaa tct ctc att cca ctt ttg gag      392
Ala Asp Lys Pro Glu Lys Ala Ala Glu Ser Leu Ile Pro Leu Leu Glu
                 55                  60                  65 gaa gct gaa gat gtt gtc cct gag gaa ctg cac ccc aag aca ccc ctt      440
Glu Ala Glu Asp Val Val Pro Glu Glu Leu His Pro Lys Thr Pro Leu
             70                  75                  80 aag ctt ggg gca aca gca ggt ttg agg ctc ttg gat ggg gat gct gct      488
Lys Leu Gly Ala Thr Ala Gly Leu Arg Leu Leu Asp Gly Asp Ala Ala
         85                  90                  95 gaa aag ata ttg caa gcg gtt agg gaa atg ttc agg aac aga agt tcc      536
Glu Lys Ile Leu Gln Ala Val Arg Glu Met Phe Arg Asn Arg Ser Ser
100                 105                 110 ctg agc gtt caa cct gat gca gta tct gtt att gat gga acc caa gaa      584
Leu Ser Val Gln Pro Asp Ala Val Ser Val Ile Asp Gly Thr Gln Glu
115                 120                 125                 130 ggt tct tac tta tgg gtt aca gtt aac tat ctg tta gga aag ttg gga      632
Gly Ser Tyr Leu Trp Val Thr Val Asn Tyr Leu Leu Gly Lys Leu Gly
                135                 140                 145 aag aag ttt aca aaa act gtg gga gtg ata gat ctt gga ggt gct tca      680
Lys Lys Phe Thr Lys Thr Val Gly Val Ile Asp Leu Gly Gly Ala Ser
            150                 155                 160 gtt caa atg gct tat gct gtc tca aga aat aca gct aaa aat gcc cca      728
Val Gln Met Ala Tyr Ala Val Ser Arg Asn Thr Ala Lys Asn Ala Pro
        165                 170                 175 aaa cca cca caa gga gag gat cca tac atg aag aag ctt gta ctc aag      776
Lys Pro Pro Gln Gly Glu Asp Pro Tyr Met Lys Lys Leu Val Leu Lys
    180                 185                 190 gga aag aaa tat gac ctt tat gtt cac agt tac ttg cgt tat ggt aac      824
Gly Lys Lys Tyr Asp Leu Tyr Val His Ser Tyr Leu Arg Tyr Gly Asn
195                 200                 205                 210 gac gca gca cgt gtt aag att ttt aag acc act gat ggt gct gct agt      872
Asp Ala Ala Arg Val Lys Ile Phe Lys Thr Thr Asp Gly Ala Ala Ser
                215                 220                 225 cct tgt cta ttg gca ggc tat gaa gat ata tac aga tat tcc gga gaa      920
Pro Cys Leu Leu Ala Gly Tyr Glu Asp Ile Tyr Arg Tyr Ser Gly Glu
            230                 235                 240 tcg tac aat atc tat ggt ccc act tct ggt gcc aac ttt aat gag tgc      968
Ser Tyr Asn Ile Tyr Gly Pro Thr Ser Gly Ala Asn Phe Asn Glu Cys
        245                 250                 255 cgt gac cta gct ctt cag att ctc aga ttg aat gag cca tgt tcc cat     1016
Arg Asp Leu Ala Leu Gln Ile Leu Arg Leu Asn Glu Pro Cys Ser His
260                 265                 270 gaa aac tgc acc ttt ggt ggg ata tgg gat ggt gga aaa gga agt gga     1064
Glu Asn Cys Thr Phe Gly Gly Ile Trp Asp Gly Gly Lys Gly Ser Gly
275                 280                 285                 290 cag aaa aac ctt gtt gtt act tca gct ttc tac tat agg tct tct gag     1112
Gln Lys Asn Leu Val Val Thr Ser Ala Phe Tyr Tyr Arg Ser Ser Glu
                295                 300                 305
```

```
gtt ggt ttt gtc act cct ccc aat tcc aaa aat cgc cct ctg gat ttt      1160
Val Gly Phe Val Thr Pro Pro Asn Ser Lys Asn Arg Pro Leu Asp Phe
            310                 315                 320 gaa act gca gct aaa caa gct tgt agt tta aca ttc gag gaa gcg aaa      1208
Glu Thr Ala Ala Lys Gln Ala Cys Ser Leu Thr Phe Glu Glu Ala Lys
        325                 330                 335 tcc act ttt cca aat gtt gag aaa gat aaa ctt cca ttt gta tgc gtg      1256
Ser Thr Phe Pro Asn Val Glu Lys Asp Lys Leu Pro Phe Val Cys Val
    340                 345                 350 gat ttc aca tac cag tat aca ttg ctt gtt gat gga ttt ggc cta gat      1304
Asp Phe Thr Tyr Gln Tyr Thr Leu Leu Val Asp Gly Phe Gly Leu Asp
355                 360                 365                 370 cca gag caa gag att aca gtg gca gaa gga att gaa tat caa gat gcc      1352
Pro Glu Gln Glu Ile Thr Val Ala Glu Gly Ile Glu Tyr Gln Asp Ala
            375                 380                 385 att gtg gaa aca gca tgg cct cta gga act gcc ata gaa gcc ata tca      1400
Ile Val Glu Thr Ala Trp Pro Leu Gly Thr Ala Ile Glu Ala Ile Ser
        390                 395                 400 tct ttg cct aaa ttt aat cgt cta atg tat ttt atc taa gccatgtcct       1449
Ser Leu Pro Lys Phe Asn Arg Leu Met Tyr Phe Ile
    405                 410                 415 ccacttatga ccactttaat taaaataaaa ctcacccttt tcactaaaaa aaaaaaaaaa    1509
aaaagtcctt ttttattcca ttgagtatca agtgttaatt tgtttctgac aaatggaggt    1569 gtaaagtga aacaaagtat gttttttgtca gatacgaatg gaagtagggt tatgatgaaa    1629
aaaaaaaaaa aaaa                                                     1643

<210> SEQ ID NO 2
<211> LENGTH: 462
<212> TYPE: PRT
<213> ORGANISM: Dolichos biflorus
<220> FEATURE:
<223> OTHER INFORMATION: lectin nucleotide phosphohydrolase (LNP, NBP46
      or DB46) root lectin

<400> SEQUENCE: 2

Met Asn Trp Val Trp Pro Lys Thr Lys Ser Met Ser Phe Leu Leu Leu
 1               5                  10                  15

Ile Thr Phe Leu Leu Phe Ser Leu Pro Lys Leu Ser Ser Ser Gln Tyr
            20                  25                  30

Val Gly Asn Ser Ile Leu Leu Asn His Arg Lys Ile Leu Pro Asn Gln
         35                  40                  45

Glu Leu Leu Thr Ser Tyr Ala Val Ile Phe Asp Ala Gly Ser Ser Gly
     50                  55                  60

Ser Arg Val His Val Phe Asn Phe Asp Gln Asn Leu Asp Leu Leu His
65                  70                  75                  80

Ile Gly Asn Asp Leu Glu Phe Thr Lys Lys Ile Lys Pro Gly Leu Ser
                85                  90                  95

Ser Tyr Ala Asp Lys Pro Glu Lys Ala Ala Glu Ser Leu Ile Pro Leu
            100                 105                 110

Leu Glu Glu Ala Glu Asp Val Val Pro Glu Glu Leu His Pro Lys Thr
        115                 120                 125

Pro Leu Lys Leu Gly Ala Thr Ala Gly Leu Arg Leu Leu Asp Gly Asp
    130                 135                 140

Ala Ala Glu Lys Ile Leu Gln Ala Val Arg Glu Met Phe Arg Asn Arg
145                 150                 155                 160
```

```
Ser Ser Leu Ser Val Gln Pro Asp Ala Val Ser Val Ile Asp Gly Thr
            165                 170                 175

Gln Glu Gly Ser Tyr Leu Trp Val Thr Val Asn Tyr Leu Leu Gly Lys
            180                 185                 190

Leu Gly Lys Lys Phe Thr Lys Thr Val Gly Val Ile Asp Leu Gly Gly
            195                 200                 205

Ala Ser Val Gln Met Ala Tyr Ala Val Ser Arg Asn Thr Ala Lys Asn
            210                 215                 220

Ala Pro Lys Pro Pro Gln Gly Glu Asp Pro Tyr Met Lys Lys Leu Val
225                 230                 235                 240

Leu Lys Gly Lys Lys Tyr Asp Leu Tyr Val His Ser Tyr Leu Arg Tyr
            245                 250                 255

Gly Asn Asp Ala Ala Arg Val Lys Ile Phe Lys Thr Thr Asp Gly Ala
            260                 265                 270

Ala Ser Pro Cys Leu Leu Ala Gly Tyr Glu Asp Ile Tyr Arg Tyr Ser
            275                 280                 285

Gly Glu Ser Tyr Asn Ile Tyr Gly Pro Thr Ser Gly Ala Asn Phe Asn
            290                 295                 300

Glu Cys Arg Asp Leu Ala Leu Gln Ile Leu Arg Leu Asn Glu Pro Cys
305                 310                 315                 320

Ser His Glu Asn Cys Thr Phe Gly Gly Ile Trp Asp Gly Gly Lys Gly
            325                 330                 335

Ser Gly Gln Lys Asn Leu Val Val Thr Ser Ala Phe Tyr Tyr Arg Ser
            340                 345                 350

Ser Glu Val Gly Phe Val Thr Pro Pro Asn Ser Lys Asn Arg Pro Leu
            355                 360                 365

Asp Phe Glu Thr Ala Ala Lys Gln Ala Cys Ser Leu Thr Phe Glu Glu
            370                 375                 380

Ala Lys Ser Thr Phe Pro Asn Val Glu Lys Asp Lys Leu Pro Phe Val
385                 390                 395                 400

Cys Val Asp Phe Thr Tyr Gln Tyr Thr Leu Leu Val Asp Gly Phe Gly
            405                 410                 415

Leu Asp Pro Glu Gln Glu Ile Thr Val Ala Glu Gly Ile Glu Tyr Gln
            420                 425                 430

Asp Ala Ile Val Glu Thr Ala Trp Pro Leu Gly Thr Ala Ile Glu Ala
            435                 440                 445

Ile Ser Ser Leu Pro Lys Phe Asn Arg Leu Met Tyr Phe Ile
450                 455                 460

<210> SEQ ID NO 3
<211> LENGTH: 1458
<212> TYPE: DNA
<213> ORGANISM: Medicago sativa
<220> FEATURE:
<221> NAME/KEY: CDS
<222> LOCATION: (1)..(1458)
<223> OTHER INFORMATION: full length clone
<221> NAME/KEY: CDS
<222> LOCATION: (13)..(1380)
<223> OTHER INFORMATION: lectin nucleotide phosphohydrolase (LNP or
      NBP46) root lectin

<400> SEQUENCE: 3 caa att aag aac atg gag ttc cta att aca ctc att gcc act ttt tta      48
Gln Ile Lys Asn Met Glu Phe Leu Ile Thr Leu Ile Ala Thr Phe Leu
  1               5                  10                  15
```

```
ctc ttg tta atg cct gca atc act tcc tcc caa tat tta gga aac aac        96
Leu Leu Leu Met Pro Ala Ile Thr Ser Ser Gln Tyr Leu Gly Asn Asn
             20                  25                  30 cta ctc act aat cga aag att ttc caa aaa caa gaa acc tta acc tct       144
Leu Leu Thr Asn Arg Lys Ile Phe Gln Lys Gln Glu Thr Leu Thr Ser
         35                  40                  45 tac gct gtc ata ttt gat gct ggt agc act ggt act cgt gtc cat gtt       192
Tyr Ala Val Ile Phe Asp Ala Gly Ser Thr Gly Thr Arg Val His Val
 50                  55                  60 tac cat ttt gat cag aac tta gat cta ctt cac att ggc aat gat att       240
Tyr His Phe Asp Gln Asn Leu Asp Leu Leu His Ile Gly Asn Asp Ile
 65                  70                  75                  80 gag ttt gtt gac aag atc aaa cca ggt ttg agt gca tat ggg gat aat       288
Glu Phe Val Asp Lys Ile Lys Pro Gly Leu Ser Ala Tyr Gly Asp Asn
                 85                  90                  95 cct gaa caa gca gca aaa tct ctc att cca ctt ttg gag gaa gca gaa       336
Pro Glu Gln Ala Ala Lys Ser Leu Ile Pro Leu Leu Glu Glu Ala Glu
            100                 105                 110 gat gtg gtt cct gag gat ctg cac ccc aaa aca ccc ctt agg ctt ggg       384
Asp Val Val Pro Glu Asp Leu His Pro Lys Thr Pro Leu Arg Leu Gly
        115                 120                 125 gca acc gca ggt ttg agg ctt ttg aat ggg gat gct gct gaa aag ata       432
Ala Thr Ala Gly Leu Arg Leu Leu Asn Gly Asp Ala Ala Glu Lys Ile
130                 135                 140 ttg caa gcg aca agg aat atg ttc agc aac aga agt acc ctc aac gtt       480
Leu Gln Ala Thr Arg Asn Met Phe Ser Asn Arg Ser Thr Leu Asn Val
145                 150                 155                 160 caa cgt gat gca gtt tct att att gat gga acc caa gaa ggt tct tat       528
Gln Arg Asp Ala Val Ser Ile Ile Asp Gly Thr Gln Glu Gly Ser Tyr
                165                 170                 175 atg tgg gtg aca gtt aac tat gta ttg ggg aat ttg gga aaa agc ttc       576
Met Trp Val Thr Val Asn Tyr Val Leu Gly Asn Leu Gly Lys Ser Phe
            180                 185                 190 aca aaa tca gtg gga gta att gac ctt gga ggt ggt tca gtt caa atg       624
Thr Lys Ser Val Gly Val Ile Asp Leu Gly Gly Gly Ser Val Gln Met
        195                 200                 205 aca tat gca gtg tca aag aaa aca gca aaa aat gct cct aaa gtt gct       672
Thr Tyr Ala Val Ser Lys Lys Thr Ala Lys Asn Ala Pro Lys Val Ala
    210                 215                 220 gat gga gag gat cca tat att aag aag ctt gtg ctc aag gga aag caa       720
Asp Gly Glu Asp Pro Tyr Ile Lys Lys Leu Val Leu Lys Gly Lys Gln
225                 230                 235                 240 tat gat ctc tat gtt cat agt tac ttg cgt ttt ggc aaa gaa gca act       768
Tyr Asp Leu Tyr Val His Ser Tyr Leu Arg Phe Gly Lys Glu Ala Thr
                245                 250                 255 cga gca cag gtt ttg aat gca act aat gga tct gct aac cct tgc att       816
Arg Ala Gln Val Leu Asn Ala Thr Asn Gly Ser Ala Asn Pro Cys Ile
            260                 265                 270 tta cct gga ttt aat ggg acc ttt aca tat tca gga gtg gag tat aag       864
Leu Pro Gly Phe Asn Gly Thr Phe Thr Tyr Ser Gly Val Glu Tyr Lys
        275                 280                 285 gct ttt tcc cct tct tct ggc tcc aac ttt gat gat tgc aaa gaa ata       912
Ala Phe Ser Pro Ser Ser Gly Ser Asn Phe Asp Asp Cys Lys Glu Ile
    290                 295                 300 att ctt aag gtt ctt aaa gta aat gat cca tgt ccc tat ccg agt tgc       960
Ile Leu Lys Val Leu Lys Val Asn Asp Pro Cys Pro Tyr Pro Ser Cys
305                 310                 315                 320
```

```
act ttt ggt gga ata tgg aat ggt gga gga ggg agt gga caa aaa aaa        1008
Thr Phe Gly Gly Ile Trp Asn Gly Gly Gly Gly Ser Gly Gln Lys Lys
                325                 330                 335 ctt ttt gtt act tca gct ttc gct tac ctg gct gaa gat gtt ggt atg        1056
Leu Phe Val Thr Ser Ala Phe Ala Tyr Leu Ala Glu Asp Val Gly Met
            340                 345                 350 gtt gag cca aat aaa cct aat tcc ata ctt cat cca gta gat ttc gaa        1104
Val Glu Pro Asn Lys Pro Asn Ser Ile Leu His Pro Val Asp Phe Glu
        355                 360                 365 att gaa gct aag cga gct tgt gca tta aac ttt gag gat gtc aaa tcc        1152
Ile Glu Ala Lys Arg Ala Cys Ala Leu Asn Phe Glu Asp Val Lys Ser
    370                 375                 380 act tat cct cga ctt acg gat gca aaa cgt cca tat gta tgc atg gat        1200
Thr Tyr Pro Arg Leu Thr Asp Ala Lys Arg Pro Tyr Val Cys Met Asp
385                 390                 395                 400 ctc tta tac caa cat gtg ttg ctt gtt cat gga ttt ggc tta ggt cca        1248
Leu Leu Tyr Gln His Val Leu Leu Val His Gly Phe Gly Leu Gly Pro
                405                 410                 415 cga aaa gag att aca gta ggt gag gga att caa tat cag aat tct gtt        1296
Arg Lys Glu Ile Thr Val Gly Glu Gly Ile Gln Tyr Gln Asn Ser Val
            420                 425                 430 gtg gaa gct gca tgg cct cta ggt act gcc gtg gaa gcc ata tca gcg        1344
Val Glu Ala Ala Trp Pro Leu Gly Thr Ala Val Glu Ala Ile Ser Ala
        435                 440                 445 tta cct aag ttt aag cga tta atg tat ttt att taa gct ttt aga gat        1392
Leu Pro Lys Phe Lys Arg Leu Met Tyr Phe Ile     Ala Phe Arg Asp
    450                 455                 460 gtc aag ata ttt cag taa cag cta act tta tca aaa att aaa taa aac        1440
Val Lys Ile Phe Gln     Gln Leu Thr Leu Ser Lys Ile Lys     Asn
465                 470                 475                 480 tgg cgc att ttg tct ttc                                                 1458
Trp Arg Ile Leu Ser Phe
                485

<210> SEQ ID NO 4
<211> LENGTH: 459
<212> TYPE: PRT
<213> ORGANISM: Medicago sativa
<220> FEATURE:
<223> OTHER INFORMATION: lectin nucleotide phosphohydrolase (LNP or
      NBP46) root lectin

<400> SEQUENCE: 4

Gln Ile Lys Asn Met Glu Phe Leu Ile Thr Leu Ile Ala Thr Phe Leu
 1               5                  10                  15

Leu Leu Leu Met Pro Ala Ile Thr Ser Ser Gln Tyr Leu Gly Asn Asn
            20                  25                  30

Leu Leu Thr Asn Arg Lys Ile Phe Gln Lys Gln Glu Thr Leu Thr Ser
        35                  40                  45

Tyr Ala Val Ile Phe Asp Ala Gly Ser Thr Gly Thr Arg Val His Val
    50                  55                  60

Tyr His Phe Asp Gln Asn Leu Asp Leu His Ile Gly Asn Asp Ile
65                  70                  75              80

Glu Phe Val Asp Lys Ile Lys Pro Gly Leu Ser Ala Tyr Gly Asp Asn
                85                  90                  95

Pro Glu Gln Ala Ala Lys Ser Leu Ile Pro Leu Leu Glu Glu Ala Glu
            100                 105                 110

Asp Val Val Pro Glu Asp Leu His Pro Lys Thr Pro Leu Arg Leu Gly
        115                 120                 125
```

```
Ala Thr Ala Gly Leu Arg Leu Leu Asn Gly Asp Ala Ala Glu Lys Ile
        130                 135                 140

Leu Gln Ala Thr Arg Asn Met Phe Ser Asn Arg Ser Thr Leu Asn Val
145                 150                 155                 160

Gln Arg Asp Ala Val Ser Ile Ile Asp Gly Thr Gln Glu Gly Ser Tyr
                165                 170                 175

Met Trp Val Thr Val Asn Tyr Val Leu Gly Asn Leu Gly Lys Ser Phe
            180                 185                 190

Thr Lys Ser Val Gly Val Ile Asp Leu Gly Gly Ser Val Gln Met
        195                 200                 205

Thr Tyr Ala Val Ser Lys Lys Thr Ala Lys Asn Ala Pro Lys Val Ala
        210                 215                 220

Asp Gly Glu Asp Pro Tyr Ile Lys Lys Leu Val Leu Lys Gly Lys Gln
225                 230                 235                 240

Tyr Asp Leu Tyr Val His Ser Tyr Leu Arg Phe Gly Lys Glu Ala Thr
                245                 250                 255

Arg Ala Gln Val Leu Asn Ala Thr Asn Gly Ser Ala Asn Pro Cys Ile
                260                 265                 270

Leu Pro Gly Phe Asn Gly Thr Phe Thr Tyr Ser Gly Val Glu Tyr Lys
            275                 280                 285

Ala Phe Ser Pro Ser Ser Gly Ser Asn Phe Asp Asp Cys Lys Glu Ile
        290                 295                 300

Ile Leu Lys Val Leu Lys Val Asn Asp Pro Cys Pro Tyr Pro Ser Cys
305                 310                 315                 320

Thr Phe Gly Gly Ile Trp Asn Gly Gly Gly Ser Gly Gln Lys Lys
                325                 330                 335

Leu Phe Val Thr Ser Ala Phe Ala Tyr Leu Ala Glu Asp Val Gly Met
                340                 345                 350

Val Glu Pro Asn Lys Pro Asn Ser Ile Leu His Pro Val Asp Phe Glu
        355                 360                 365

Ile Glu Ala Lys Arg Ala Cys Ala Leu Asn Phe Glu Asp Val Lys Ser
370                 375                 380

Thr Tyr Pro Arg Leu Thr Asp Ala Lys Arg Pro Tyr Val Cys Met Asp
385                 390                 395                 400

Leu Leu Tyr Gln His Val Leu Leu Val His Gly Phe Gly Leu Gly Pro
                405                 410                 415

Arg Lys Glu Ile Thr Val Gly Glu Gly Ile Gln Tyr Gln Asn Ser Val
            420                 425                 430

Val Glu Ala Ala Trp Pro Leu Gly Thr Ala Val Glu Ala Ile Ser Ala
            435                 440                 445

Leu Pro Lys Phe Lys Arg Leu Met Tyr Phe Ile
        450                 455

<210> SEQ ID NO 5
<211> LENGTH: 9
<212> TYPE: PRT
<213> ORGANISM: Medicago sativa

<400> SEQUENCE: 5

Ala Phe Arg Asp Val Lys Ile Phe Gln
 1               5

<210> SEQ ID NO 6
<211> LENGTH: 8
<212> TYPE: PRT
```

-continued

```
<213> ORGANISM: Medicago sativa

<400> SEQUENCE: 6

Gln Leu Thr Leu Ser Lys Ile Lys
  1               5

<210> SEQ ID NO 7
<211> LENGTH: 7
<212> TYPE: PRT
<213> ORGANISM: Medicago sativa

<400> SEQUENCE: 7

Asn Trp Arg Ile Leu Ser Phe
  1               5

<210> SEQ ID NO 8
<211> LENGTH: 1489
<212> TYPE: DNA
<213> ORGANISM: Lotus japonicus
<220> FEATURE:
<221> NAME/KEY: CDS
<222> LOCATION: (1)..(1488)
<223> OTHER INFORMATION: full length clone
<221> NAME/KEY: CDS
<222> LOCATION: (43)..(1413)
<223> OTHER INFORMATION: lectin nucleotide phosphohydrolase (LNP or
      NBP46) root lectin

<400> SEQUENCE: 8 aag tgc tct tct ctc tgt agt tag ttg cat tgg act aaa gcc atg gac      48
Lys Cys Ser Ser Leu Cys Ser     Leu His Trp Thr Lys Ala Met Asp
  1               5                      10                  15 ttc tta att agt ctc atg acc ttt gtg ttc atg tta atg cct gct atc      96
Phe Leu Ile Ser Leu Met Thr Phe Val Phe Met Leu Met Pro Ala Ile
             20                  25                  30 tct tcc tcc caa tat ctc gga aac aac att ctc atg aat cgt aag ata     144
Ser Ser Ser Gln Tyr Leu Gly Asn Asn Ile Leu Met Asn Arg Lys Ile
         35                  40                  45 tta ctc ccc aaa aat cag gaa cca gtt aca tca tac gct gtt ata ttt     192
Leu Leu Pro Lys Asn Gln Glu Pro Val Thr Ser Tyr Ala Val Ile Phe
     50                  55                  60 gat gct ggt agc act gga agc aga gtc cat gtc tac aat ttt gat cag     240
Asp Ala Gly Ser Thr Gly Ser Arg Val His Val Tyr Asn Phe Asp Gln
 65                  70                  75                  80 aac tta gat ctc ctt ccc gtt gaa aac gaa ctt gag ttt tat gat tcg     288
Asn Leu Asp Leu Leu Pro Val Glu Asn Glu Leu Glu Phe Tyr Asp Ser
                 85                  90                  95 gtt aaa ccc ggt ttg agt tca tac gct gct aat cct gaa gaa gct gca     336
Val Lys Pro Gly Leu Ser Ser Tyr Ala Ala Asn Pro Glu Glu Ala Ala
            100                 105                 110 gaa tct ctg att cca ctt cta aaa gaa gca gaa aat gtg gtt cct gtg     384
Glu Ser Leu Ile Pro Leu Leu Lys Glu Ala Glu Asn Val Val Pro Val
        115                 120                 125 agc cag caa ccc aac aca ccc gtt aag ctt ggg gca act gca ggt tta     432
Ser Gln Gln Pro Asn Thr Pro Val Lys Leu Gly Ala Thr Ala Gly Leu
    130                 135                 140 agg ctt ttg gag ggg aat gct gct gaa aat ata ttg caa gcg gtc agg     480
Arg Leu Leu Glu Gly Asn Ala Ala Glu Asn Ile Leu Gln Ala Val Arg
145                 150                 155                 160 gat atg ctc agc aac aga agt gcc ctt aat gtt caa tca gat gca gta     528
Asp Met Leu Ser Asn Arg Ser Ala Leu Asn Val Gln Ser Asp Ala Val
                165                 170                 175
```

```
tct att ctt gat gga acc caa gaa ggt tct tat ctt tgg gtg aca att      576
Ser Ile Leu Asp Gly Thr Gln Glu Gly Ser Tyr Leu Trp Val Thr Ile
        180                 185                 190 aac tat ctc ttg ggg aag ttg gga aaa aga ttt aca aag aca gtg gga      624
Asn Tyr Leu Leu Gly Lys Leu Gly Lys Arg Phe Thr Lys Thr Val Gly
            195                 200                 205 gta gtt gat cta gga ggt ggg tca gtg caa atg aca tat gca gtc tca      672
Val Val Asp Leu Gly Gly Gly Ser Val Gln Met Thr Tyr Ala Val Ser
        210                 215                 220 agg aac aca gct aaa aat gct cca aaa gta cct gaa gga gag gat cca      720
Arg Asn Thr Ala Lys Asn Ala Pro Lys Val Pro Glu Gly Glu Asp Pro
225                 230                 235                 240 tac ata aag aag ctt gta ctc cag gga aag aaa tat gac ctt tat gtt      768
Tyr Ile Lys Lys Leu Val Leu Gln Gly Lys Lys Tyr Asp Leu Tyr Val
                245                 250                 255 cac agt tac ttg cgc tat gga aga gaa gca ttt cgt gca gag att ttc      816
His Ser Tyr Leu Arg Tyr Gly Arg Glu Ala Phe Arg Ala Glu Ile Phe
            260                 265                 270 aag gtc gct ggt ggt tct gct aat cct tgc att tta gct ggc ttt gat      864
Lys Val Ala Gly Gly Ser Ala Asn Pro Cys Ile Leu Ala Gly Phe Asp
        275                 280                 285 ggg gca tat aca tat tcc gga gca gag tat aag gtc tcg gcc cca gct      912
Gly Ala Tyr Thr Tyr Ser Gly Ala Glu Tyr Lys Val Ser Ala Pro Ala
290                 295                 300 tca gga tct aac ttg aat caa tgc aga aag ata gct ctt aag gct ctt      960
Ser Gly Ser Asn Leu Asn Gln Cys Arg Lys Ile Ala Leu Lys Ala Leu
305                 310                 315                 320 aaa gtg aat gca cct tgt ccc tat cag aat tgc act ttt ggt ggg ata     1008
Lys Val Asn Ala Pro Cys Pro Tyr Gln Asn Cys Thr Phe Gly Gly Ile
                325                 330                 335 tgg aat ggt gga ggt gga agt ggt caa aaa aat ctt ttc ctt act tca     1056
Trp Asn Gly Gly Gly Gly Ser Gly Gln Lys Asn Leu Phe Leu Thr Ser
            340                 345                 350 tct ttc tat tac ctc tct gaa gat gtt ggg atc ttt gtg aat aaa ccc     1104
Ser Phe Tyr Tyr Leu Ser Glu Asp Val Gly Ile Phe Val Asn Lys Pro
        355                 360                 365 aat gcc aaa att cgt cca gtt gat ttg aag act gca gct aaa cta gct     1152
Asn Ala Lys Ile Arg Pro Val Asp Leu Lys Thr Ala Ala Lys Leu Ala
    370                 375                 380 tgt aaa aca aat ctt gag gat gca aaa tcc aaa tac cca gat ctt tat     1200
Cys Lys Thr Asn Leu Glu Asp Ala Lys Ser Lys Tyr Pro Asp Leu Tyr
385                 390                 395                 400 gag aaa gac agt gtt gaa tat gtg tgc ttg gat ctt gtc tac gtg tac     1248
Glu Lys Asp Ser Val Glu Tyr Val Cys Leu Asp Leu Val Tyr Val Tyr
                405                 410                 415 aca ttg ctt gtt gat gga ttt ggt ctt gat cca ttt caa gag gtt aca     1296
Thr Leu Leu Val Asp Gly Phe Gly Leu Asp Pro Phe Gln Glu Val Thr
            420                 425                 430 gtg gcg aat gaa att gaa tat cag gat gct ctt gtg gaa gcc gca tgg     1344
Val Ala Asn Glu Ile Glu Tyr Gln Asp Ala Leu Val Glu Ala Ala Trp
        435                 440                 445 cct cta ggc act gcc ata gaa gca ata tca tca ttg cct aaa ttt gag     1392
Pro Leu Gly Thr Ala Ile Glu Ala Ile Ser Ser Leu Pro Lys Phe Glu
    450                 455                 460 aga tta atg tat ttt att taa act act agt acc tgc tta agc ctg gat     1440
Arg Leu Met Tyr Phe Ile     Thr Thr Ser Thr Cys Leu Ser Leu Asp
465                 470                 475                 480
```

```
tac ctg aag aaa taa aat gaa ata aaa gcc gca tct ttc ttc ctt gct t    1489
Tyr Leu Lys Lys     Asn Glu Ile Lys Ala Ala Ser Phe Phe Leu Ala
                485                 490                 495
```

<210> SEQ ID NO 9
<211> LENGTH: 7
<212> TYPE: PRT
<213> ORGANISM: Lotus japonicus

<400> SEQUENCE: 9

```
Lys Cys Ser Ser Leu Cys Ser
 1               5
```

<210> SEQ ID NO 10
<211> LENGTH: 462
<212> TYPE: PRT
<213> ORGANISM: Lotus japonicus
<220> FEATURE:
<223> OTHER INFORMATION: lectin nucleotide phosphohydrolase (LNP or
      NBP46) root lectin

<400> SEQUENCE: 10

```
Leu His Trp Thr Lys Ala Met Asp Phe Leu Ile Ser Leu Met Thr Phe
 1               5                  10                  15

Val Phe Met Leu Met Pro Ala Ile Ser Ser Ser Gln Tyr Leu Gly Asn
                20                  25                  30

Asn Ile Leu Met Asn Arg Lys Ile Leu Leu Pro Lys Asn Gln Glu Pro
            35                  40                  45

Val Thr Ser Tyr Ala Val Ile Phe Asp Ala Gly Ser Thr Gly Ser Arg
        50                  55                  60

Val His Val Tyr Asn Phe Asp Gln Asn Leu Asp Leu Leu Pro Val Glu
 65                  70                  75                  80

Asn Glu Leu Glu Phe Tyr Asp Ser Val Lys Pro Gly Leu Ser Ser Tyr
                85                  90                  95

Ala Ala Asn Pro Glu Glu Ala Ala Glu Ser Leu Ile Pro Leu Leu Lys
            100                 105                 110

Glu Ala Glu Asn Val Val Pro Val Ser Gln Gln Pro Asn Thr Pro Val
        115                 120                 125

Lys Leu Gly Ala Thr Ala Gly Leu Arg Leu Leu Glu Gly Asn Ala Ala
130                 135                 140

Glu Asn Ile Leu Gln Ala Val Arg Asp Met Leu Ser Asn Arg Ser Ala
145                 150                 155                 160

Leu Asn Val Gln Ser Asp Ala Val Ser Ile Leu Asp Gly Thr Gln Glu
                165                 170                 175

Gly Ser Tyr Leu Trp Val Thr Ile Asn Tyr Leu Leu Gly Lys Leu Gly
            180                 185                 190

Lys Arg Phe Thr Lys Thr Val Gly Val Asp Leu Gly Gly Gly Ser
        195                 200                 205

Val Gln Met Thr Tyr Ala Val Ser Arg Asn Thr Ala Lys Asn Ala Pro
    210                 215                 220

Lys Val Pro Glu Gly Glu Asp Pro Tyr Ile Lys Lys Leu Val Leu Gln
225                 230                 235                 240

Gly Lys Lys Tyr Asp Leu Tyr Val His Ser Tyr Leu Arg Tyr Gly Arg
                245                 250                 255

Glu Ala Phe Arg Ala Glu Ile Phe Lys Val Ala Gly Gly Ser Ala Asn
            260                 265                 270
```

```
Pro Cys Ile Leu Ala Gly Phe Asp Gly Ala Tyr Thr Tyr Ser Gly Ala
        275                 280                 285

Glu Tyr Lys Val Ser Ala Pro Ala Ser Gly Ser Asn Leu Asn Gln Cys
    290                 295                 300

Arg Lys Ile Ala Leu Lys Ala Leu Lys Val Asn Ala Pro Cys Pro Tyr
305                 310                 315                 320

Gln Asn Cys Thr Phe Gly Gly Ile Trp Asn Gly Gly Gly Ser Gly
                325                 330                 335

Gln Lys Asn Leu Phe Leu Thr Ser Ser Phe Tyr Tyr Leu Ser Glu Asp
            340                 345                 350

Val Gly Ile Phe Val Asn Lys Pro Asn Ala Lys Ile Arg Pro Val Asp
        355                 360                 365

Leu Lys Thr Ala Ala Lys Leu Ala Cys Lys Thr Asn Leu Glu Asp Ala
    370                 375                 380

Lys Ser Lys Tyr Pro Asp Leu Tyr Glu Lys Asp Ser Val Glu Tyr Val
385                 390                 395                 400

Cys Leu Asp Leu Val Tyr Val Tyr Thr Leu Leu Val Asp Gly Phe Gly
                405                 410                 415

Leu Asp Pro Phe Gln Glu Val Thr Val Ala Asn Glu Ile Glu Tyr Gln
            420                 425                 430

Asp Ala Leu Val Glu Ala Ala Trp Pro Leu Gly Thr Ala Ile Glu Ala
        435                 440                 445

Ile Ser Ser Leu Pro Lys Phe Glu Arg Leu Met Tyr Phe Ile
    450                 455                 460

<210> SEQ ID NO 11
<211> LENGTH: 13
<212> TYPE: PRT
<213> ORGANISM: Lotus japonicus

<400> SEQUENCE: 11

Thr Thr Ser Thr Cys Leu Ser Leu Asp Tyr Leu Lys Lys
1               5                   10

<210> SEQ ID NO 12
<211> LENGTH: 11
<212> TYPE: PRT
<213> ORGANISM: Lotus japonicus

<400> SEQUENCE: 12

Asn Glu Ile Lys Ala Ala Ser Phe Phe Leu Ala
1               5                   10

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:degenerate
      5' PCR primer
<221> NAME/KEY: modified_base
<222> LOCATION: (6)
<223> OTHER INFORMATION: n = g, a, c or t
<221> NAME/KEY: modified_base
<222> LOCATION: (9)
<223> OTHER INFORMATION: n = g, a, c or t
```

```
<400> SEQUENCE: 13
taygcngtna tyttygatcg                                                20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:degenerate
      3' PCR primer
<221> NAME/KEY: modified_base
<222> LOCATION: (15)
<223> OTHER INFORMATION: n = g, a, c or t

<400> SEQUENCE: 14
atrttrtada trccngg                                                   17
```